(12) United States Patent
Motterle et al.

(10) Patent No.: US 8,680,276 B2
(45) Date of Patent: Mar. 25, 2014

(54) SYNTHESIS OF (4AS,7AS)-OCTAHYDRO-1H-PYRROLO[3,4-B]PYRIDINE

(76) Inventors: Riccardo Motterle, Vicenza (IT); Giancarlo Arvotti, Vicenza (IT); Elisabetta Bergantino, Padua (IT); Andrea Castellin, Padua (IT); Stefano Fogal, Treviso (IT); Marco Galvagni, Verona (IT)

( * ) Notice: Subject to any disclaimer, the term of this patent is extended or adjusted under 35 U.S.C. 154(b) by 227 days.

(21) Appl. No.: 13/056,458

(22) PCT Filed: Mar. 4, 2010

(86) PCT No.: PCT/EP2010/052734
§ 371 (c)(1),
(2), (4) Date: Feb. 18, 2011

(87) PCT Pub. No.: WO2010/100215
PCT Pub. Date: Sep. 10, 2010

(65) Prior Publication Data
US 2011/0137036 A1 Jun. 9, 2011

(30) Foreign Application Priority Data
Mar. 6, 2009 (IT) .............................. MI2009A0332

(51) Int. Cl.
*C07D 211/34* (2006.01)
(52) U.S. Cl.
USPC ............................ 546/116; 546/238; 546/183
(58) Field of Classification Search
USPC .......................................... 546/115, 238, 183
See application file for complete search history.

(56) References Cited

FOREIGN PATENT DOCUMENTS

EP 0 550 903 A1 7/1993
WO WO 99/09200 A1 2/1999

OTHER PUBLICATIONS

Chemical Abstract Services Sep. 1, 2009, Registry No. 1178858-33-7.*
Chemical Abstract Services Jul. 29, 2009, Registry No. 1169974-48-4.*
C. Agami et al., "Neuromediator analogs: synthesis of cis (2R, 3S) and trans (2S, 3S)-2, 3-piperidine dicarboxylic acids from (2S)-2-phenylglycinol", *Tetrahedron Letters*, vol. 36, No. 10, Jan. 10, 1995, pp. 1657-1660.
C. Agami et al., "Enantioselective synthesis of comfortionally restricted analogs of NMDA: cis- and trans-piperdine-2, 3-dicarboxylic acids and methylated derivatives", *Journal of Organic Chemistry*, vol. 61, No. 17, pp. 5736-5742, 1996.

* cited by examiner

*Primary Examiner* — David K O Dell

(57) ABSTRACT

The present invention relates to the stereoselective synthesis of (4aS,7aS)-octahydro-1H-pyrrolo[3,4-b]pyridine, as well as the conversion thereof, to give Moxifloxacin. Particularly, the present invention relates to a method for the synthesis of (4aS,7aS)-octahydro-1H-pyrrolo[3,4-b]pyridine of formula (I) comprising: (a) the optical resolution by enzymatic hydrolysis of the intermediate dialkyl-1-alkylcarbonylpiperidine-2,3-dicarboxylate racemate of formula (II) to give, following isolation, the intermediate dialkyl-(2S,3R)-1-alkylcarbonyl-piperidine-2,3-dicarboxylate of formula (III) in which Alk is a straight or branched C1-C5 alkyl group; (b) the conversion of the intermediate (III) to (4aR,7aS)-1-alkylcarbonylhexahydrofuro[3,4-b]pyridine-5,7-dione of formula (IV) in which Alk has the meanings set forth above; (c) the conversion of the intermediate (IV) to (4aS,7as)-octahydro-1H-pyrrolo[3,4-b]pyridine of formula (I) with an optical purity above 99%.

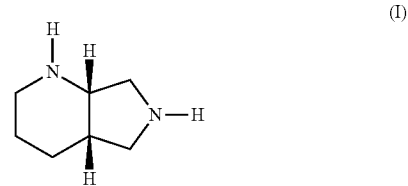

(I)

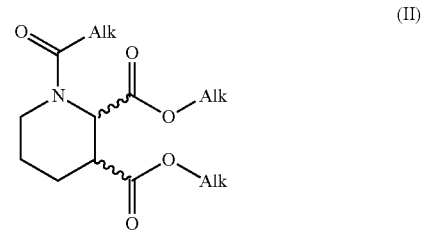

(II)

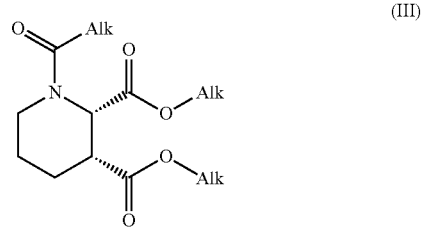

(III)

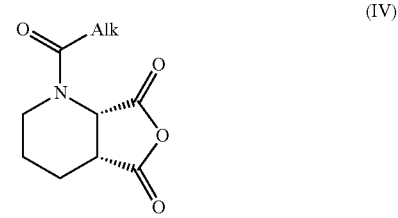

(IV)

7 Claims, 4 Drawing Sheets

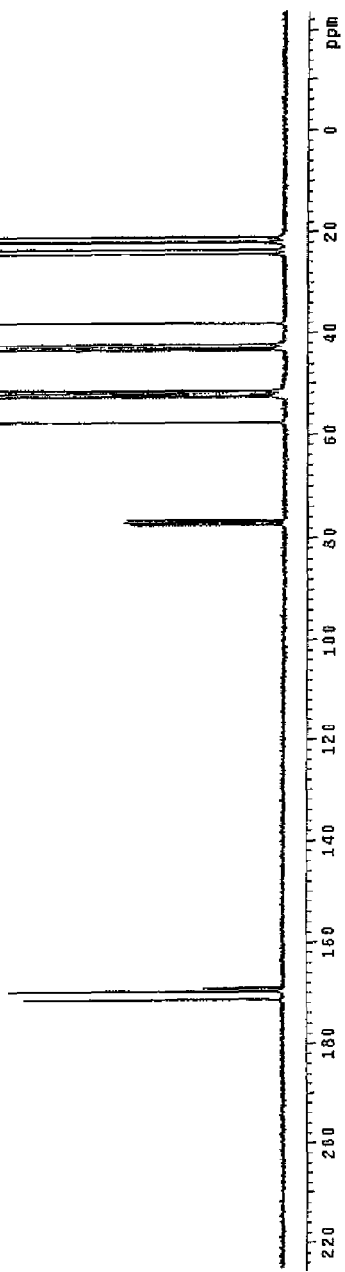

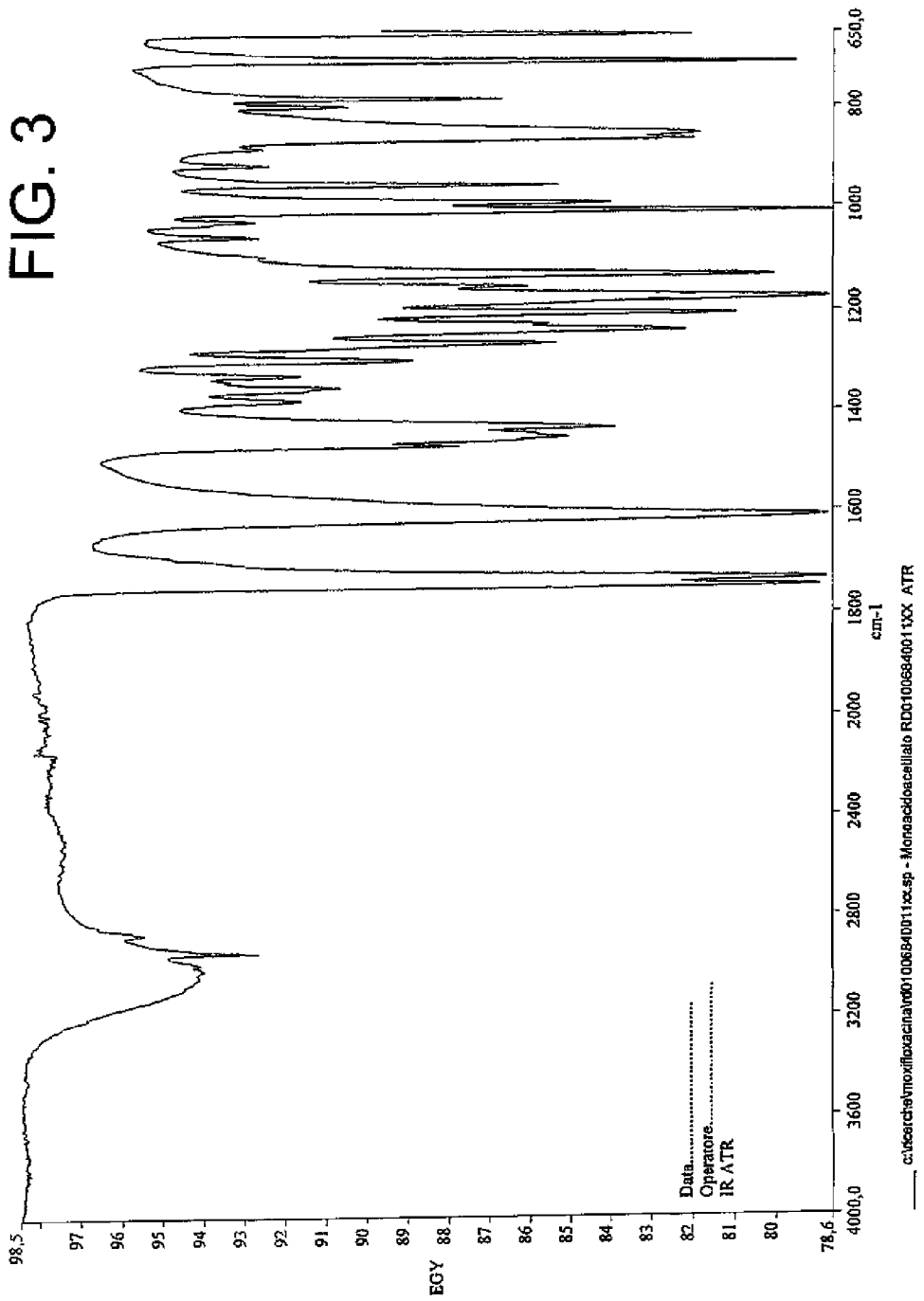

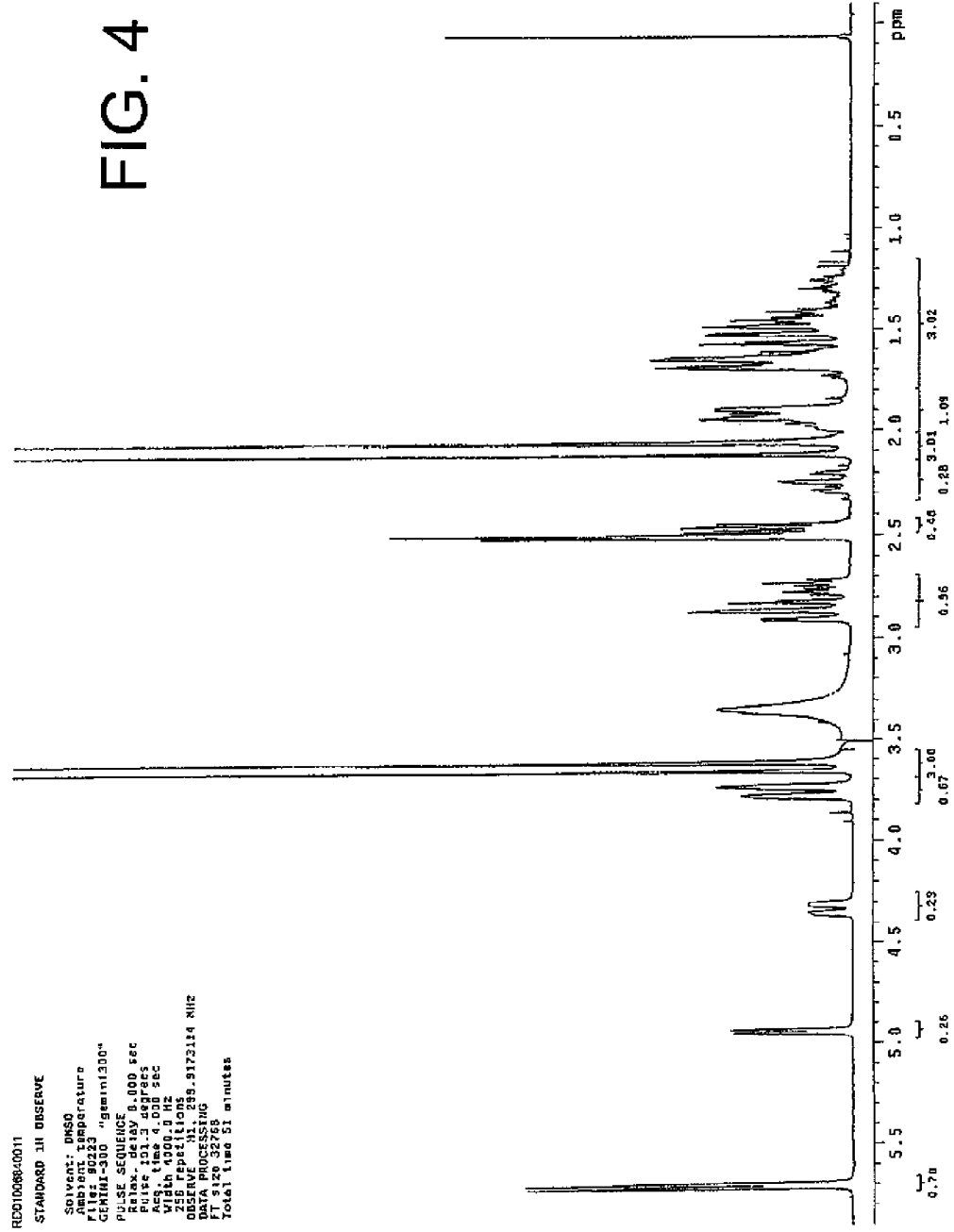

SYNTHESIS OF (4AS,7AS)-OCTAHYDRO-1H-PYRROLO[3,4-B] YRIDINE

The present invention relates to the stereoselective synthesis of (4aS,7aS)-octahydro-1H-pyrrolo[3,4-b]pyridine, as well as the conversion thereof to give Moxifloxacin.

STATE OF THE ART

Moxifloxacin is a synthetic broadspectrum antibacterial agent, employed for the treatment of respiratory infections (pneumonia, chronic sinusitis, chronic bronchitis), skin and soft tissues. Clinical trials are also being carried out in which Moxifloxacin is used in the treatment of tuberculosis. Moxifloxacin, a fluoroquinolone, is available as the monohydrochloride salt of 1-cyclopropyl-7-[(S,S)-2,8-diazabycyclo[4.3.0]non-8-yl]-6-fluoro-8-methoxy-1,4-dihydro-4-oxo-3-quinoline carboxylic acid. Moxifloxacin is commercialized with the tradename of Avelox® and, in a low-dosage form for ophthalmic use, with the tradename of Vigamox®.

The molecule is characterized by a fluoroquinolonic skeleton, which is common to that of other two antibiotics of the same category (Gatifloxacin and Balofloxacin) and by a side chain S,S-diazabicyclononane:

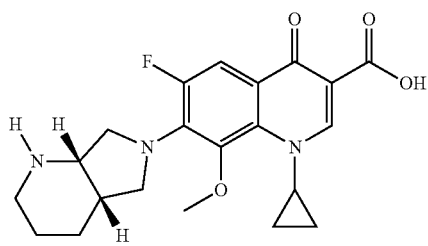 [SMILES: COc1c(N2C[C@@H]3CCCN[C@@H]3C2)c(F)cc2c(=O)c(C(=O)O)cn(C3CC3)c12]

The intermediate fluoroquinolone (CAS No.: 112811-72-0), with or without the methoxy group, is a commercial product, the synthesis of which requires eleven steps. The involved chemistry is common to most fluoroquinolons.

The S,S-diazabicyclononane or (S,S)-2,8-diazabycyclo[4.3.0]nonane or (4aS,7aS)-octahydro-1H-pyrrolo[3,4-b]pyridine (CAS No.: 151213-40-0) is the most critical intermediate, since it has two chiral centres, both of configuration S, is optically active and levogyre. It is also a commercial substance, but the synthesis and optical resolution thereof is currently not satisfactory.

The condensation of the two above-mentioned synthons, the intermediate fluoroquinolone, with or without methoxy substituent and the intermediate S,S-diazabicyclononane, is carried out with methods that are known and reported, for example, in the patent publications EP 0 350 733 A1, EP 0 757 990 A1, EP 0 550 903 A1, EP 1 034 173 A1, WO 2006/052264, WO 2005/012285, WO 2006/134491, and EP 1 832 587 A1.

The synthesis of the intermediate S,S-diazabicyclononane of the prior art comprises the reaction of pyridine-2,3-dicarboxylic acid anhydride with benzyl amine to give N-benzyl-2,3-pyridine-dicarboxamide, the reduction of the pyridine ring to give 6-benzyl-5,7-dioxooctahydropyrrolo[3,4-b]pyridine, the reduction of the amide groups to give 6-benzyloctahydropyrrolo[3,4-b]pyridine, and the optical resolution thereof by formation of the diastereoisomeric salt with L-tartaric acid, followed by debenzylation. This route of synthesis is described, for example, in EP 0 550 903 A1, EP 1 077 979 A1, and in the article Zhongguo Yiyao Gongye Zazhi 2004, 35, 129. However, the enantiomeric excess is not satisfactory.

Alternatively, the optical resolution of the intermediate 6-benzyl-5,7-dioxooctahydropyrrolo[3,4-b]pyridine with D-tartaric acid has been described, followed by the reduction of the amide groups, and subsequently by debenzylation. The method is described in EP 0 550 903 A1, EP 1 067 129 A1, EP 1 192 153 A1, and EP 1 375 501 A1, and also in this case it leads to low enantiomeric excesses.

Finally, in EP 1 003 902 A1 the enzymatic resolution of the diazabicyclononane racemate is described, by means of a transesterification reaction with ethyl acetate in the presence of a lipase from *Candida antarctica*. However, the reaction proceeds very slowly, requiring 14 days at a temperature of 40° C.

SUMMARY OF THE INVENTION

Therefore, the problem that is addressed by the present invention is to provide an alternative process for the preparation of the intermediate (4aS,7aS)-octahydro-1H-pyrrolo[3,4-b]pyridine in an optically active form with high enantiomeric excess.

Such problem is solved by a synthesis method of (4aS,7aS)-octahydro-1H-pyrrolo[3,4-b]pyridine as set forth in the annexed claims, the definitions of which form an integral part of the present description.

BRIEF DESCRIPTION OF THE FIGURES

FIG. 2 shows a $^{13}$C NMR spectrum (in CDCl3, 300 MHz) of the intermediate (III);

FIG. 3 shows an IR spectrum of the intermediate (X);

FIG. 4 shows a proton NMR spectrum (in CDCl3, 300 MHz) of the intermediate (X).

DETAILED DESCRIPTION OF THE INVENTION

Figure 1:
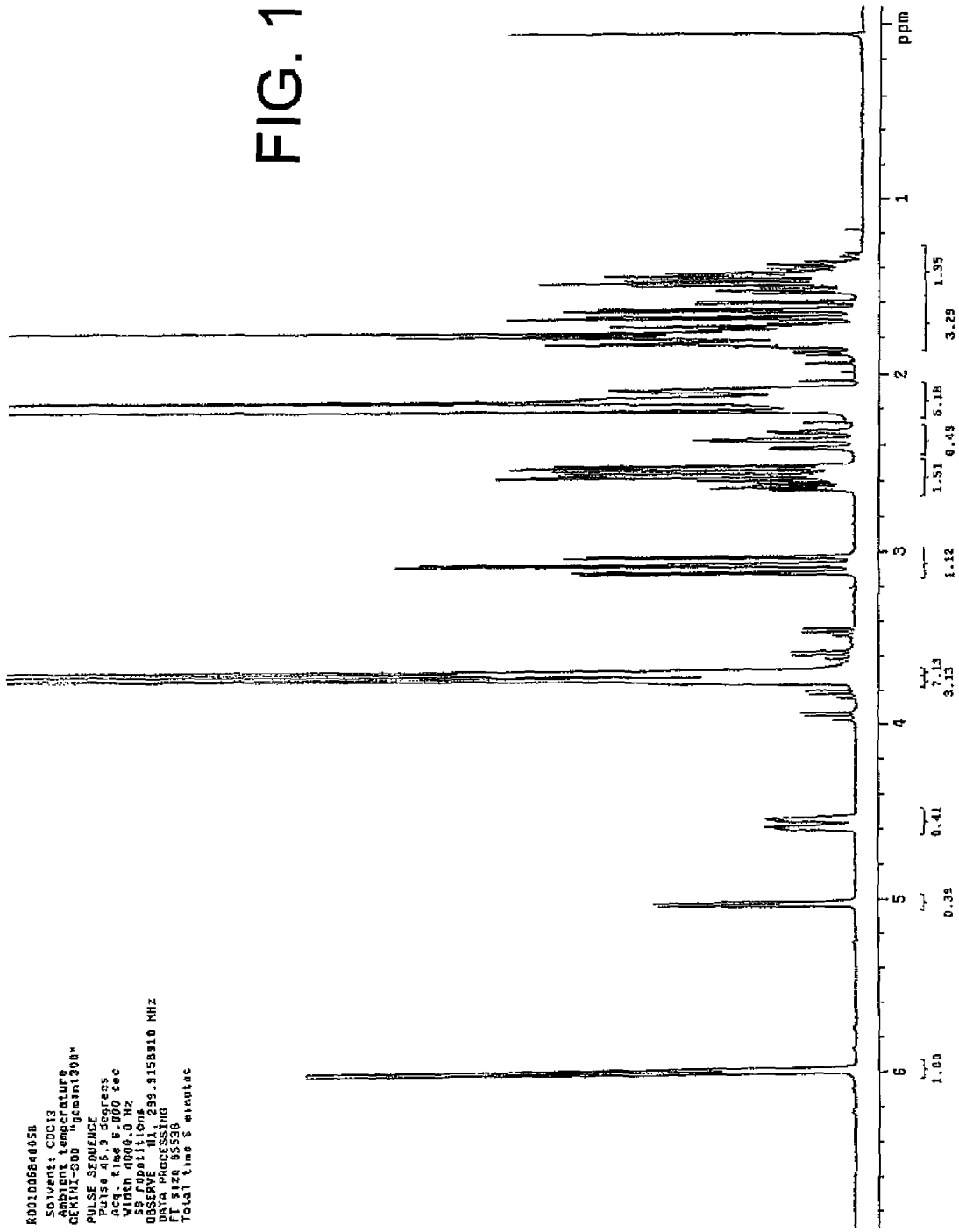
FIG. 1 shows a proton NMR spectrum (in CDCl3, 300 MHz) of the intermediate (III)

The present invention relates to the synthesis of (4aS,7aS)-octahydro-1H-pyrrolo[3,4-b]pyridine of formula (I):

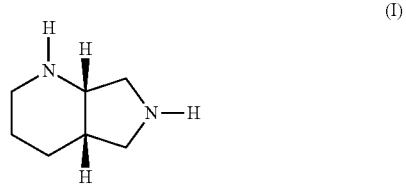

according to the following method, which provides for:

(a) the optical resolution by enzymatic hydrolysis of the intermediate dialkyl-1-alkylcarbonylpiperidine-2,3-dicarboxylate racemate of formula (II)

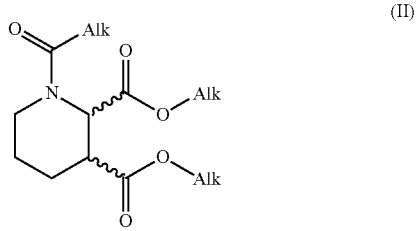

(II)

thanks to the action of a lipase or an esterase, to give, after isolating the intermediate (2S,3R)-1-alkylcarbonylpiperidine-2,3-dialkyldicarboxylate of formula (III):

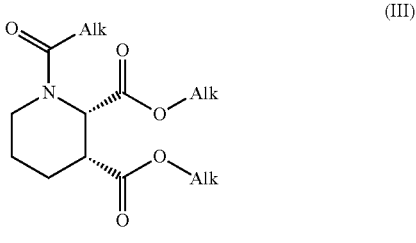

(III)

in which Alk is a straight or branched C1-C5 alkyl group;
(b) the conversion of the intermediate (III) to (4aR,7aS)-1-alkylcarbonylhexahydrofuro[3,4-b]pyridine-5,7-dione of formula (IV):

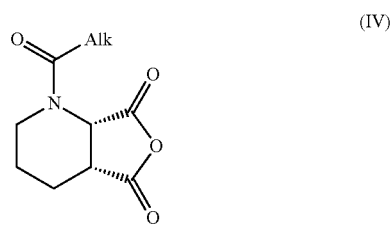

(IV)

in which Alk has the meanings set forth above;
(c) the conversion of the intermediate (IV) to (4aS,7aS)-octahydro-1H-pyrrolo[3,4-b]pyridine of formula (I) with optical purity above 99%.

In an embodiment, the optical resolution by enzymatic hydrolysis of the intermediate dialkyl-1-alkylcarbonylpiperidine-2,3-dicarboxylate racemate of formula (II) (step (a)) is carried out by means of a lipase or an esterase. In a particular embodiment, such lipase is lipase B of *Candida antarctica* (CALB), preferably in an immobilized form on an inert solid support, particularly lipase B covalently immobilized on beads of polyacrylates. Such product is commercial, and it can be obtained according to conventional methods. Alternatively, lipase B in a form entrapped in porous gel or in a non-immobilized form will be able to be used. The use of the enzyme in the immobilized form has the advantage to allow an easy recycling and reuse of the same.

In a different embodiment, said esterase is PLE.

The reaction can be carried out, both batch-wise and in flow, in water or mixtures of water and an organic solvent, such as DMSO, acetonitrile, N-MPO, solutions of surfactants (Triton), heptanes, at a temperature ranging between 20° C. and 40° C., preferably at 25-35° C., more preferably about 30° C., and for a period of time ranging between 70 and 200 hours, preferably between 100 and 200 hours, more preferably between 130 and 150 hours. It is suitable that the pH of the solution is maintained at about pH=6.

The Alk group in formula (II), (III) and (X) of the ester functional group can be the same or also different of that of the amidic group. The Alk group in formula (II), (III) and (X) is preferably a methyl. The optical resolution reaction takes place according to the following scheme A:

Scheme A

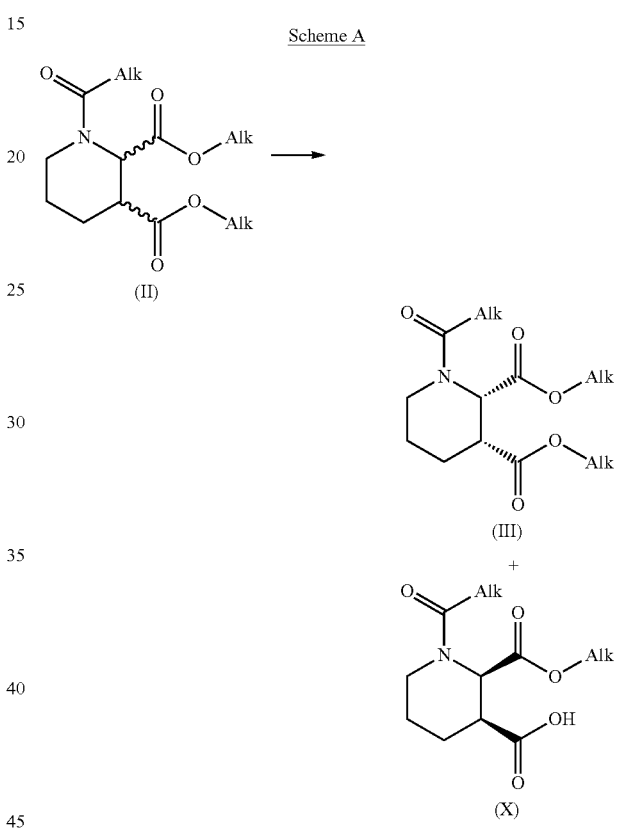

The enzyme selectively hydrolyses the isomer (2R,3S) providing the intermediate of formula (X), which can be divided from the mixture and isolated by solubilization with a base and reprecipitation or isolation in the presence of an acid, according to conventional methods.

Instead, the desired isomer (2S,3R) (intermediate of formula (III)) is isolated from the reaction mixture by extraction with an organic solvent. In an embodiment, a strong base will be used, such as, for example, a 30% NaOH solution in water, up to pH 8, the aqueous phase will be washed with an organic solvent until extraction of the diester (verified by HPLC), then the pH of the aqueous solution will be brought back to a pH of about 7, for example, with a strong acid, such as aqueous HCl, thus separating the intermediate (X). Instead, the combined organic phases will provide, by evaporation to dryness, the desired intermediate (III).

In an embodiment, the conversion of the intermediate (III) to (4aR,7aS)-1-alkylcarbonylhexahydrofuro[3,4-b]pyridine-5,7-dione of formula (IV) (step (b)) is carried out in two stages:

(b1) hydrolysis of the amide and ester alkylcarbonyl group to give the intermediate (2S,3R)-piperidine-2,3-dicarboxylic acid of formula (IIIa):

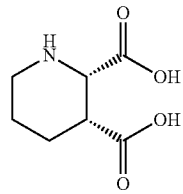

(IIIa)

(b2) cyclization of the intermediate (IIIa) to give the intermediate (IV).

The stage (b1) can be carried out by treatment with a strong acid. For example, aqueous HCl under reflux for a period of time ranging between 2 and 4 hours will be able to be used.

The stage (b2) can be carried out by reaction of the intermediate (IIIa) with a condensing agent, such as an anhydride. For example, an acetic anhydride/acetic acid mixture, or pure acetic anhydride at a temperature ranging between 90° C. and 120° C., preferably about 110° C., will be able to be used.

In an embodiment, the conversion of the intermediate (IV) to (4aS,7as)-octahydro-1H-pyrrolo[3,4-b]pyridine of formula (I) (step (c)) can be carried out in four stages:

(c1) reaction of the intermediate (IV) with a primary amine GP-NH2 to give an imide of formula (IVa), 6-substituted-(4aR,7aS)-1-alkylcarbonyltetrahydro-1H-pyrrolo[3,4-b]pyridine-5,7(2H,6H)-dione, in which the nitrogen of the imide is substituted with an easily removable substituent:

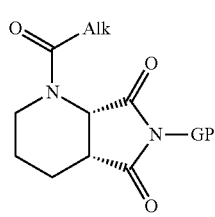

(IVa)

in which Alk is as defined above, and GP is a protective group preferably selected from benzyl amine or benzyl amine substituted, for example, with alkyl, p-nitro, fluorine, trifluoromethyl in the ortho or para position;

(c2) removal of the alkyl carbonyl group on the piperidine nitrogen to give the intermediate of formula (IVb):

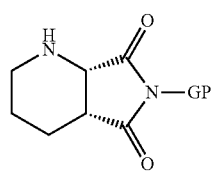

(IVb)

in which GP is as defined above;

(c3) reduction of the imide functionality to give the intermediate of formula (IVc):

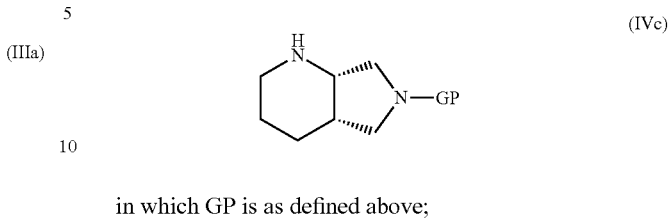

(IVc)

in which GP is as defined above;

(c4) removal of the protective group GP to give the intermediate of formula (I).

The stage (c1) can be carried out in an inert solvent, for example, toluene, at temperatures ranging between 50° C. and the boiling temperature of the solvent, preferably between 70° C. and 100° C.

The stage (c2) can be carried out by treatment with a strong acid, for example, hydrochloric acid under reflux for a period of time ranging between 4 hours and 10 hours.

The stage (c3) can be carried out with an alkaline metal hydride, such as, for example, LiAlH4.

The stage (c4) can be carried out by catalytic hydrogenation, for example, in the presence of a suitable Pd/C catalyst. Suitably, it will be possible to operate at a temperature ranging between 40° C. and 80° C., and under pressures ranging between 2 and 50 bars.

The final intermediate of formula (I) can be isolated with enantiomeric purity above 98%, or above 99%, by distillation of the reaction mixture, preferably by vacuum distillation.

The intermediate of formula (II):

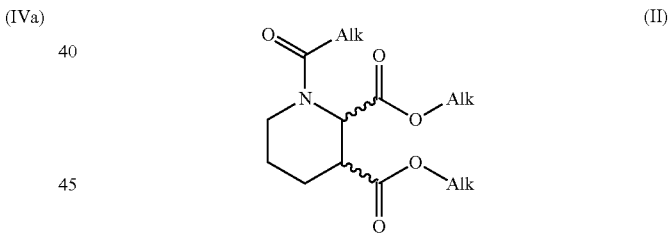

(II)

can be prepared starting from pyridine-2,3-dicarboxylic acid, commercially available, by a method which provides for the following steps:

(i) esterification of the pyridine-2,3-dicarboxylic acid to give dialkyl-pyridine-2,3-dicarboxylate of formula (V):

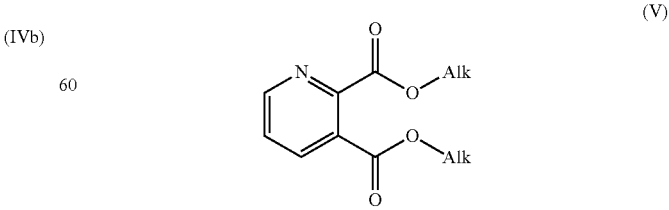

(V)

in which Alk is a straight or branched C1-C5 alkyl group;

(ii) reduction of the intermediate (V) in a substantially anhydrous environment to give dialkyl-piperidine-2,3-dicarboxylate racemate of formula (VI):

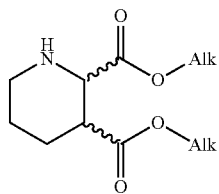

(VI)

in which Alk is as defined above;

(iii) reaction of alkylcarbonylation of the intermediate (VI) to give the intermediate (II), in which Alk is as defined above.

In the step (i), the Alk group is preferably methyl. The reaction can be carried out, for example, in methanol with catalysis of strong acid, for example, hydrochloric acid, under reflux for a period of time ranging between 15 hours and 40 hours, preferably between 20 and 30 hours.

The reduction step (ii) can be carried out by catalytic hydrogenation. A useful catalyst is Pd/C at a temperature ranging between 40° C. and 80° C. and a pressure between 5 and 20 bars. The reaction environment has to be substantially anhydrous, to prevent the formation of trans isomers.

In the step (iii), Alk is preferably methyl. The acylation reaction can be carried out by using acetic anhydride with basic catalysis, preferably of organic bases, such as tertiary amines.

The reduction step (ii) provide exclusively the racemic mixture of the 2,3-sostituents in configuration cis and therefore the mixture of (2S,3R) and (2R,3S)-piperidine-2,3-dialkyldicarboxylate, also named cis-piperidine-2,3-dialkyldicarboxylate, excluding the other two enantiomers of configuration trans named (2S,3S) and (2R,3R)-piperidine-2,3-dialkyldicarboxylate.

The step (iii) provide therefore the intermediate of formula (II) dialkyl-1-alkylcarbonylpiperidine-2,3-dicarboxylate racemate which is a mixture of (2S,3S) and (2R,3R)-1-alkylcarbonylpiperidine-2,3-dialkyldicarboxylate where the substituents in positions 2 and 3 are in configuration cis. The compound of formula (II) could therefore also be named cis-dialkyl-1-alkylcarbonylpiperidine-2,3-dicarboxylate racemate or cis-1-alkylcarbonylpiperidine-2,3-dialkyldicarboxylate racemate. The intermediate (I) that is obtained as described above can be converted into Moxifloxacin according to the two following synthesis routes.

Process A

The first synthesis route provides for the following steps:

(A1) condensation reaction of the intermediate (I) with a fluoroquinolone of formula (VII):

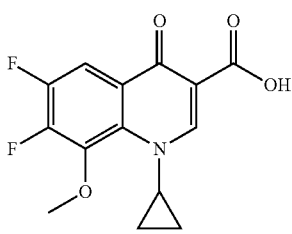

(VII)

to give moxifloxacin, free base;

(B1) optionally, salification with hydrogen chloride to give moxifloxacin hydrochloride.

Process B

The second synthesis route provides for the following steps:

(A2) condensation of the intermediate (I) with a fluoroquinolone of formula (VIII):

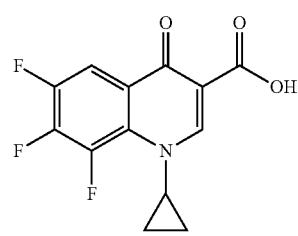

(VIII)

to give the intermediate of formula (IX):

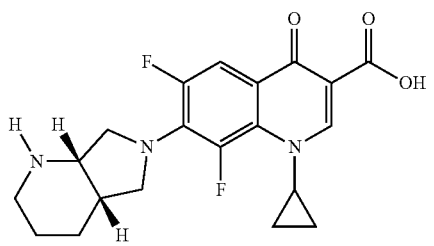

(IX)

(B2) methoxylation of the intermediate (IX) to give Moxifloxacin free base;

(C2) optionally, salification with hydrogen chloride to give moxifloxacin hydrochloride.

The conversions indicated herein above for the processes A and B can be obtained according to methods known to those skilled in the art, such as those described in the patent publications EP 0 350 733 A1, EP 0 757 990 A1, EP 0 550 903 A1, EP 1 034 173 A1, WO 2006/052264, WO 2005/012285, WO 2006/134491, and EP 1 832 587 A1.

As stated above, the method of the invention, and particularly the enzymatic reduction step set forth above, allows also obtaining the intermediate of formula (X), (2R,3S)-1-alkylcarbonyl-2-(alkoxycarbonyl)piperidine-3-carboxylic acid, and preferably, (2R,3S)-1-acetyl-2-(methoxycarbonyl)piperidine-3-carboxylic acid, in an enantiomerically pure form (enantiomeric purity >99%). Such intermediate of formula (X), although not falling within the synthesis process of moxifloxacin, is a synthon of interest. For example, it can be used for the preparation of pyrrolidinecarboxyamide compounds and piperidinecarboxyamides functionalized with quinoline-methoxyphenylsulfonylmethyl radicals that can be used as inhibitors of MMP, TNF, and aggrecanase, described in the patent publication WO 2002/055491.

The enantiomer (2R,3S) of the intermediate (III), (2R,3S)-1-alkylcarbonylpiperidine-2,3-dialkyldicarboxylate having formula (III-bis)

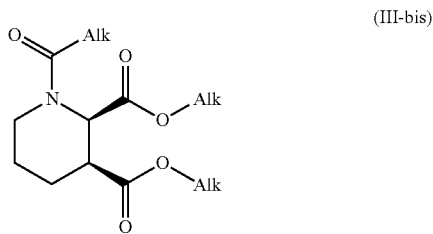

(III-bis)

which can be obtained by esterification of the compound of formula (X) or according Example 11, can be instead used for the synthesis of ligands for the preparation of compounds with activity of modulators of the histamine receptor H4, as described in the patent publications WO 2008/100656, WO 2008/008359, and WO 2007/072163.

Moreover, the intermediate (2R,3S)-1-alkylcarbonyl-2-(alkoxycarbonyl)piperidine-3-carboxylic acid of formula (X) can be conveniently converted in the key intermediate (4aR,7aR)-octahydro-1H-pyrrolo[3,4-b]pyridine of formula (XII):

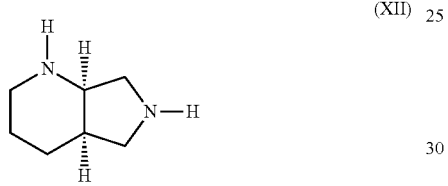

(XII)

also known as (R,R)-2,8-Diazabicyclo[4.3.0]nonane or R,R-diazabicyclononane having CAS RN 151213-42-2. Such key intermediate is actually employed for the synthesis of other active pharmaceutical ingredients as described in the patent publications EP591808 (antibiotics), WO2005054239 (histamine H4 antagonists for the treatment of asthma) and WO2008067871 (substituted dihydropyrazolones for treating cardiovascular and haematological diseases).

Therefore, it is a further object a method for the preparation of the intermediate of formula (X) as defined above, as well as such intermediate (X) as a synthon of pharmacologically active compounds.

According to an embodiment of the present invention, the process for the preparation of (4aR,7aR)-octahydro-1H-pyrrolo[3,4-b]pyridine of formula (XII) comprises:

(a) the optical resolution by enzymatic hydrolysis of the intermediate dialkyl-1-alkylcarbonylpiperidine-2,3-dicarboxylate racemate of formula (II)

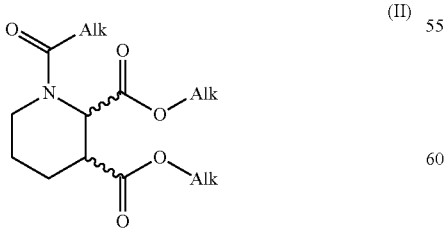

(II)

thanks to the action of a lipase or an esterase to give the intermediate (2R,3S)-1-alkylcarbonyl-2-(alkoxycarbonyl) piperidine-3-carboxylic acid of formula (X):

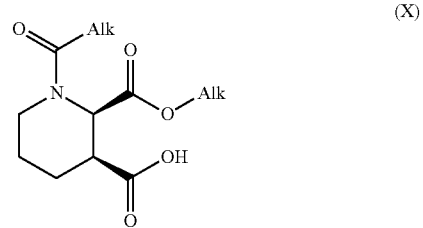

(X)

in which Alk is a straight or branched C1-C5 alkyl group;

(b) the conversion of the intermediate (X) to (4aS,7aR)-1-alkylcarbonylhexahydrofuro[3,4-b]pyridine-5,7-dione of formula (IV-bis):

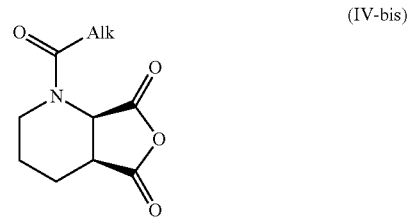

(IV-bis)

in which Alk has the meanings set forth above;

(c) the conversion of the intermediate (IV-bis) to (4aR,7aR)-octahydro-1H-pyrrolo[3,4-b]pyridine of formula (XII).

The R,R-diazabicyclononane so prepared showed an optical purity higher than 99%.

In an embodiment, the conversion of the intermediate (X) to (4aS,7aR)-1-alkylcarbonylhexahydrofuro[3,4-b]pyridine-5,7-dione of formula (IV-bis) (step (b)) is carried out in two stages:

(b1) hydrolysis of the amide and ester alkylcarbonyl group to give the intermediate (2R,3S)-piperidine-2,3-dicarboxylic acid of formula (IIIa-bis):

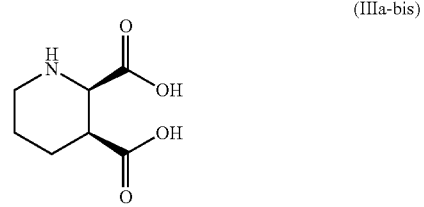 [SMILES: O=C(O)[C@H]1CCCN[C@H]1C(=O)O]

(IIIa-bis)

(b2) cyclization of the intermediate (IIIa-bis) to give the intermediate (IV-bis).

The conversion of the intermediate of formula (X)

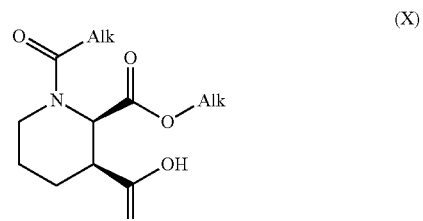

(X)

to the compound (2R,3S)-1-piperidine-2,3-dicarboxylic acid of formula (IIIa-bis), (IIIa-bis)

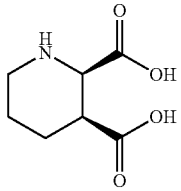

as hydrochloride salt, which is the enantiomer of the compound (IIIa) previously described, could be conveniently performed according to the same procedure disclosed in Example 2 for preparation of the compound IIIa.
The conversion of the intermediate (IIIa-bis) to the compound of formula (IV-bis)

(IV-bis)

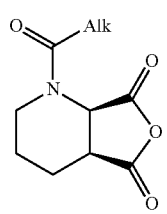

and then to (4aR,7aR)-octahydro-1H-pyrrolo[3,4-b]pyridine of formula (XII)

(XII)

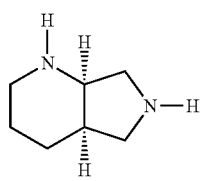

passing through the compound 6-substituted-(4aS,7aR)-1-alkylcarbonyltetrahydro-1H-pyrrolo[3,4-b]pyridine-5,7(2H,6H)-dione of formula (IVa-bis):

(IVa-bis)

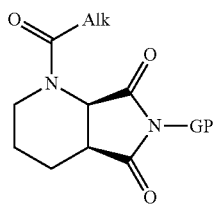

in which Alk and GP have the same meanings of compound IVa was experimentally carried out by performing exactly the same process and procedures described in the examples 3-7, that conversely relate to the S,S-enantiomer.

As described in Example 1, the isolated compound (2R,3S)-1-alkylcarbonyl-2-(alkoxycarbonyl)piperidine-3-carboxylic acid of formula (X) undergoes to internal transesterification reaction according the following scheme:

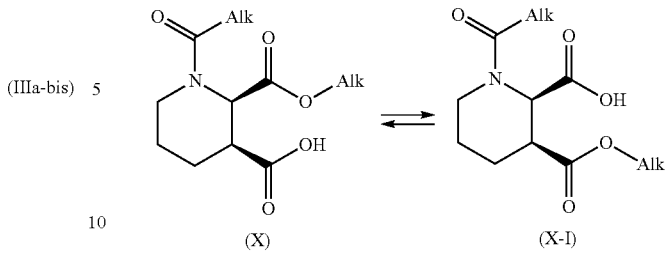

providing also the isomer (2R,3S)-1-alkylcarbonyl-3-(alkoxycarbonyl)piperidine-2-carboxylic acid derivatives of formula (X-I).

An advantage of the invention is the preparation of the core of piperidine-2,3-disubstituted compounds having an absolute configuration (one optical isomers of four) in a very easy, practical and almost quantitative way, providing optical purity equal to or higher of 99% and avoiding the recycle of conventional resolution agents. The invention therefore allows also the practical preparation of new compounds such as those of formula III, X-bis, X-bis-I, IV, IVa, X, X-I, III-bis, IV-bis, IVa-bis and known compounds like IIIa and IIIa-bis. These last two compounds (2S,3R)-piperidine-2,3-dicarboxylic acids and (2R,3S)-piperidine-2,3-dicarboxylic acids and related hydrochloride salts have been prepared only by a quite complex and long enantioselective synthesis as described in Journal of Organic Chemistry (1996), 61(17), pag. 5736-5742 Tetrahedron Letters (1995), 36(10), pag. 1657-60 and they were used as neuromediator analogs.

In an embodiment, the process for the preparation of (2S,3R)-piperidine-2,3-dicarboxylic acid of formula (IIIa)

(IIIa)

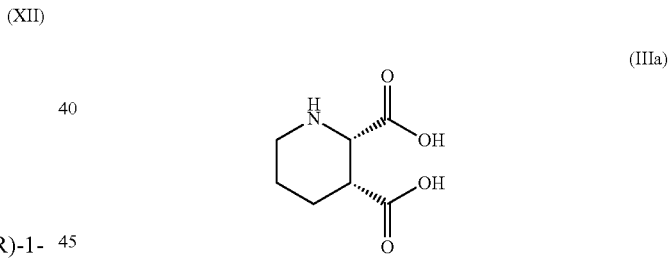

comprises the following steps:

(a) the optical resolution by enzymatic hydrolysis of the intermediate dialkyl-1-alkylcarbonylpiperidine-2,3-dicarboxylate racemate of formula (II)

(II)

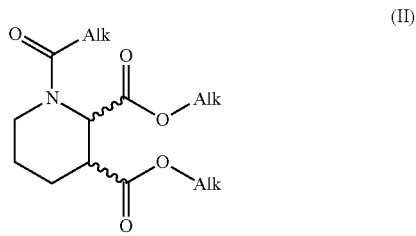

thanks to the action of a lipase or an esterase to give the intermediate (2S,3R)-1-alkylcarbonylpiperidine-2,3-dialkyldicarboxylate of formula (III):

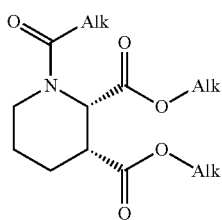

(III)

in which Alk is a straight or branched C1-C5 alkyl group;

(b) the conversion of the intermediate (III) to (2S,3R)-piperidine-2,3-dicarboxylic acid of formula (IIIa) by means of acid hydrolysis.

In the examples 1 and 2 is described in detail the experimental procedure.

According to an embodiment of the present invention, the process for the preparation of (2R,3S)-piperidine-2,3-dicarboxylic acid of formula (IIIa-bis)

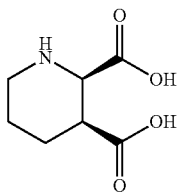

(IIIa-bis)

comprises the following steps:

(a) the optical resolution by enzymatic hydrolysis of the intermediate dialkyl-1-alkylcarbonylpiperidine-2,3-dicarboxylate racemate of formula (II)

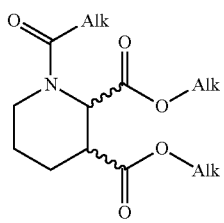

(II)

thanks to the action of a lipase or an esterase to give the intermediate (2R,3S)-1-alkylcarbonyl-2-(alkoxycarbonyl)piperidine-3-carboxylic acid of formula (X):

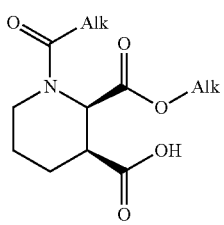

(X)

in which Alk is a straight or branched C1-C5 alkyl group;

(b) the conversion of the intermediate (X) to (2R,3S)-piperidine-2,3-dicarboxylic acid of formula (IIIa-bis) by means of acid hydrolysis.

In the examples 1 and 2 is described in detail the experimental procedure.

EXPERIMENTAL SECTION

Preparation 1

Synthesis of the Intermediate (V) (Alk=Me)

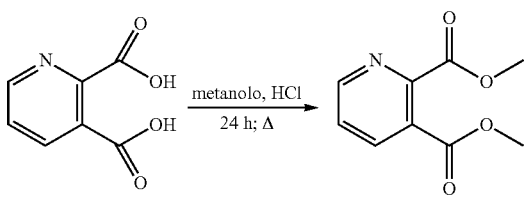

RN: 89-00-9
acido piridin-2,3-dicarbossilico dimetil piridin-2,3-dicarbossilato

METANOLO = methanol
ACIDO PIRIDIN-2,3-DICARBOSSILICO = pyridine-2,3-dicarboxylic acid
DIMETIL PIRIDIN-2,3-DICARBOSSILATO = dimethyl-pyridine-2,3-dicarboxylate In a 1 L three-necked flask equipped with mechanical stirrer and oil bath, 100 g pyridine-2,3-dicarboxylic acid, 1000 mL 15% hydrochloric acid solution in anhydrous methanol are loaded, and it is heated under reflux for 22 hours following the course of the reaction via HPLC. Once the conversion was complete, the reaction is cooled, and a residue is concentrated under reduced pressure, then it is taken up with 400 mL toluene. 300 mL of 10% sodium carbonate aqueous solution up to pH 8 is added dropwise under stirring. The phases are divided, and the aqueous phase is extracted again with 100 mL toluene. The combined organic phases are washed with 50 ml water. The toluene phase is anhydrified by distilling toluene up to a final volume of 400 mL. The obtained solution is used directly in the successive reaction.

Preparation 2

Synthesis of the Intermediate (VI) (Alk=Me)

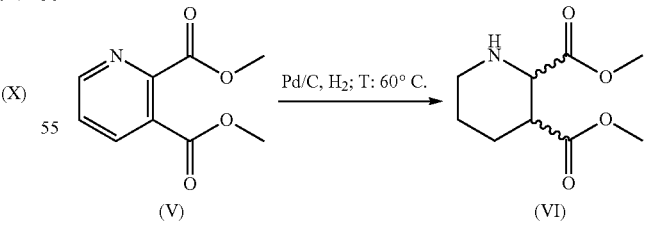

(V)          (VI)

In a 3 L steel autoclave, the toluene solution (about 400 mL) of the preparation 1 is added, virtually containing 116.8 g intermediate (V), and 2 g 10% Pd/C (anhydrous) is added. Then, it is hydrogenated at 60° C. and 10 bars for about 4 hours. Once the reaction was completed (monitored via GC), the catalyst is filtered off and the toluene solution that is obtained is directly used in the following step.

NOTE: the hydrogenation is cis-stereospecific, and it allows obtaining the pair of cis enantiomers without the trans pair. The absence of water is crucial to prevent the racemization to C2.

Preparation 3

Synthesis of the Intermediate (II) (Alk=Me)

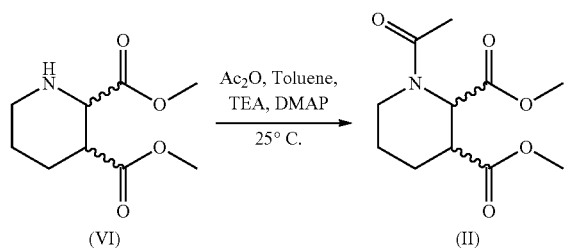

In a 500 mL three-necked flask equipped with mechanical stirrer and oil bath, the toluene solution (about 400 mL) containing virtually 120.5 g intermediate (VI), 80 mL triethyl amine, 5.3 g dimethylaminopyridine (DMAP) are added. Under stirring at 25-30° C., 57 mL acetic anhydride are added in 30 min. It is stirred at 25° C. for 2.5 hours. Once the conversion was complete (monitored by GC analysis), the mass is quenched by adding about 30 mL of 5% sodium bicarbonate aqueous solution. The phases are divided, and the organic phase is washed with 2×20 mL of 5% sodium bicarbonate aqueous solution. The combined aqueous phases are washed with 3×100 mL toluene. Finally, the combined organic phases are washed with 20 ml water. The organic phase is concentrated under reduced pressure. The obtained residue is taken up with 280 mL MTBE. It is heated to complete dissolution, then it is cooled at T.A. and then at 10° C. by stirring for 2 hours. The obtained crystal (the possible trans diastereoisomer remains almost completely dissolved in the mother liquors) is filtered off by washing with 2×30 mL of cold MTBE. The reaction is dried at 35° C. in a ventilated oven, thus obtaining 95 g of product as a white crystal. Total yield (3 steps)=65.3%, equal to an average yield for each step of about 87%. GC titre: 99.7% (A %); trans diastereoisomer, about 0.02%.

Example 1

Synthesis of the Intermediate (III) (Alk=Me)

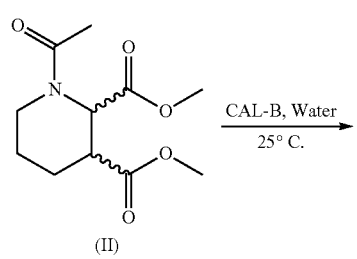

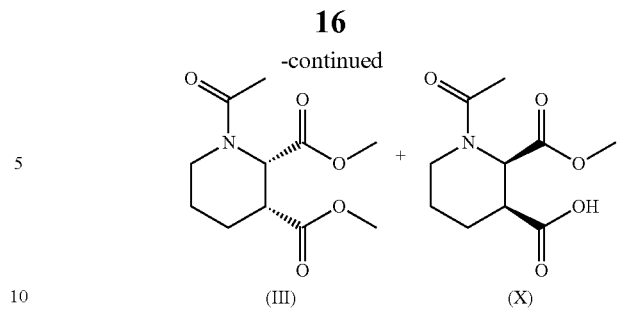

In a 1 L jacketed reactor with mechanical stirrer, thermostat, and automatic titrator loaded with an aqueous solution of 0.1 M NaOH, 80 g intermediate (II), 400 mL buffer solution at pH 6 (50 mM phosphate buffer), and 40 g CALB-T2-150 Chiralvision, batch 48107227 (enzyme CAL-B covalently immobilized on polyacrylic matrix beads) are added. The reaction is stirred at 35° C. for about 140 hours maintaining the pH at about 6 thanks to the addition of 32.3 mL of a 0.1 M NaOH solution. The course of the reaction is followed via chiral HPLC. Once the conversion is complete, the enzyme is filtered off for further reuse. The solution is combined to an analogous mixture, which is obtained again starting from 80 g intermediate (II) and in which the recycled enzyme has been used. The total aqueous phase obtained (about 1000 mL) is brought to pH 7 and concentrated to a small volume (about 350 mL). Then it is brought to pH 8 with 8 mL of 30% NaOH. The reaction is extracted with 3×500 mL ethyl acetate. The diester (2S,3R enantiomer, intermediate (III)) remains in the organic phase, while the monoacid (2R,3S enantiomer, intermediate (X)) remains in the aqueous phase. The chemical purity of the two phases is verified via HPLC by carrying out, if needed, a counter-extraction (with water for the organic phase, and ethyl acetate for the aqueous phase) to remove optional residues of the undesired species.

ISOLATION OF ENANTIOMER (2S,3R)-1-acetylpiperidine-2,3-dimethyldicarboxylate (Intermediate (III))

The organic phase (ethyl acetate) is concentrated to a residue obtaining 86 g of (2S,3R)-1-acetylpiperidine-2,3-dimethyldicarboxylate (the desired enantiomer for the synthesis of Moxifloxacin) with a chiral purity of 99%. The yield is slightly above the theoretical one, due to the presence of ethyl acetate/water residues. The proton NMR and 13C spectra (in CDCl3, 300 MHz) of the compound (III) are shown in FIGS. 1 and 2, respectively.

ISOLATION OF ENANTIOMER (2R,3S)-1-acetyl-2-(methoxycarbonyl)piperidine-3-carboxylic acid (Intermediate (X))

The aqueous phase is brought back to pH 7 with conc. HCl and is concentrated to residue, thus obtaining 115 g of a pale yellow oil containing a variable amount of inorganic salts (partially precipitated) and possibly of water. Chiral HPLC purity (A %): 99.17% monoacid enantiomer.

A study by H-NMR, COSY, HMQC, HMBC allowed to assign which ester position is hydrolysed by the enzyme and therefore to clarify the structure of the molecule (X).

The IR and proton NMR spectra (in CDCl3, 300 MHz) of the isolated compound (X) are shown in FIGS. 3 and 4, respectively. The spectra reveal the presence of a monoester mixture in the 2 and 3 positions, due to internal transesterification reactions according the following scheme

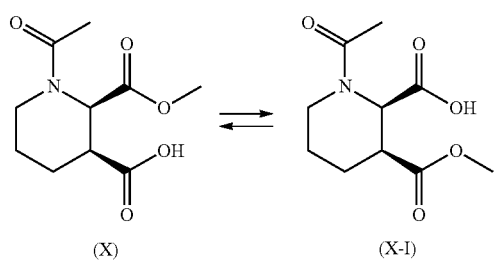

The isomer compound (2R,3S)-1-acetyl-3-(methoxycarbonyl)piperidine-2-carboxylic acid of formula X-I is therefore obtained from the compound of formula X.

Example 2

Synthesis of the Intermediate (IIIa) (Hydrochloride)

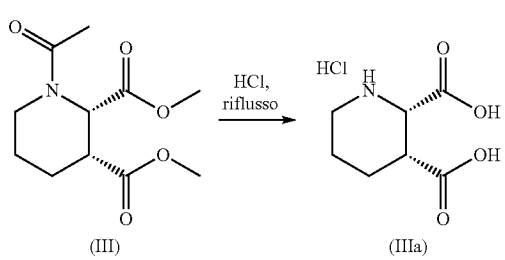

In a 1 L three-necked flask equipped with mechanical stirrer and oil bath, 115 g of raw intermediate (III) and 400 mL concentrated HCl are loaded, and it is heated under reflux for 8 hours. Once the complete conversion is verified via HPLC, it is concentrated to residue, thus obtaining the product with the optional presence of inorganic salts.

Example 3

Synthesis of the Intermediate (IV) (Alk=Me)

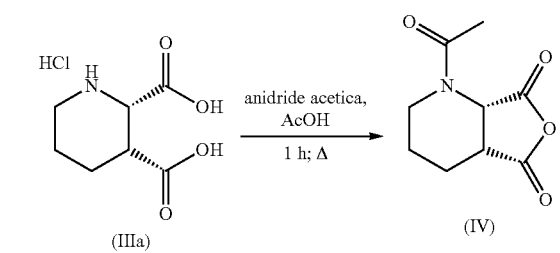

ANIDRIDE ACETICA = acetic anhydride

In a 250 mL three-necked flask equipped with mechanical stirrer and oil bath, 26 g raw intermediate (IIIa), and 50 mL acetic anhydride are loaded. It is heated at 110° C. for about 3 hours. Once the reaction is complete (followed by HPLC), it is cooled at 70° C. and 100 mL toluene are added. If necessary, the obtained solution is filtered to remove the optional salts that are present, and it is used directly in the successive step.

Example 4

Synthesis of the Intermediate (IVa) (Alk=Me, GP=benzyl)

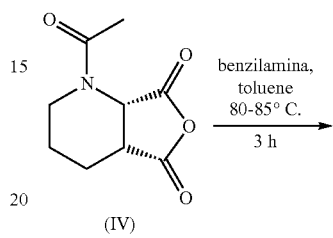

BENZILAMINA = benzylamine

The solution deriving from the preceding step is brought to 70° C. Then, 38 mL benzylamine are added dropwise. The reaction is held at 70° C. for about 2 hours. Once the reaction is complete (verification of conversion via GC), 30 ml water is added. The reaction is stirred, and the phases are separated. The aqueous phase is extracted again with 4×20 mL toluene. The combined organic phases are brought to residue obtaining 34.5 g of the desired product as an oil.

Example 5

Synthesis of the Intermediate (IVb) (hydrochloride, GP=benzyl)

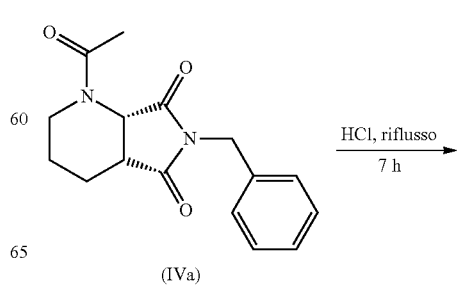

-continued

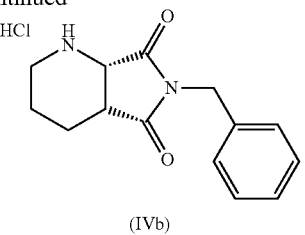

RIFLUSSO = reflux

In a 250 mL three-necked flask equipped with mechanical stirrer and oil bath, 28.5 g raw intermediate (IVa) and 60 mL concentrated hydrochloric acid are loaded. It is heated under reflux for about 7 hours. Once the reaction is complete (followed by HPLC), it is cooled, and 30 ml water and 1 g active carbon is added. It is heated to 60° C., and filtered on Dicalite by washing with 30 ml water. It is concentrated to residue under reduced pressure, then it is taken up with 15 mL toluene. It is concentrated to residue and taken up again with 15 mL toluene. It is concentrated to residue, thus obtaining 27 g of a hazel crystal.

Example 6

Synthesis of the Intermediate (IVc) (GP=benzyl)

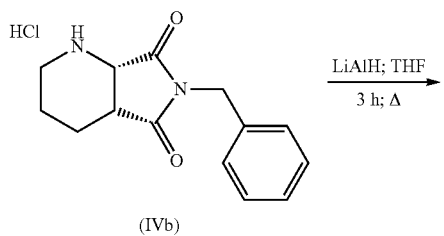

are filtered by washing with 2×30 mL THF. It is concentrated to residue, thus obtaining 11.2 g oil.

Example 7

Synthesis of the Compound (I)

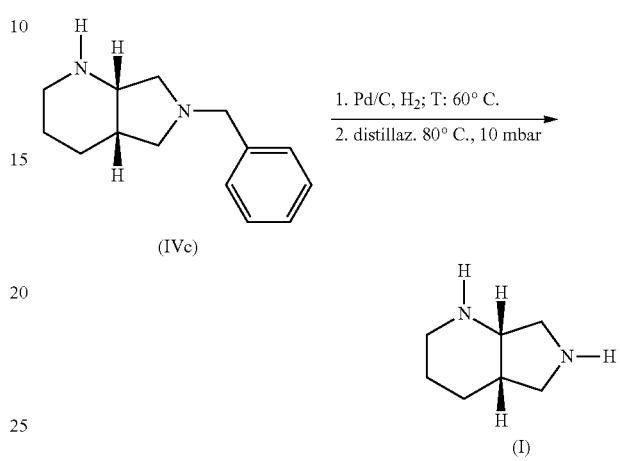

DISTILLAZ. = distillation

In a 500 mL steel autoclave, 11.2 g raw intermediate (IVc), 90 mL methanol, and 1.2 g of dry 10% Pd/C are loaded. The reaction is heated to 60° C. by hydrogenation at 30 bar for about 9 hours. Once the reaction is complete (followed by GC), the catalyst is filtered off and concentrated to residue, thus obtaining 8 g oil. The latter is purified by distillation at 9 mbar and 115° C., thus obtaining the compound (1).

The reaction of the examples 2-7 can be repeated starting from the intermediate (X), thus obtaining, if desired, the other enantiomer of the compound (1).

Example 8

Synthesis of the Intermediate (III) (Alk=Me) with Free Enzyme

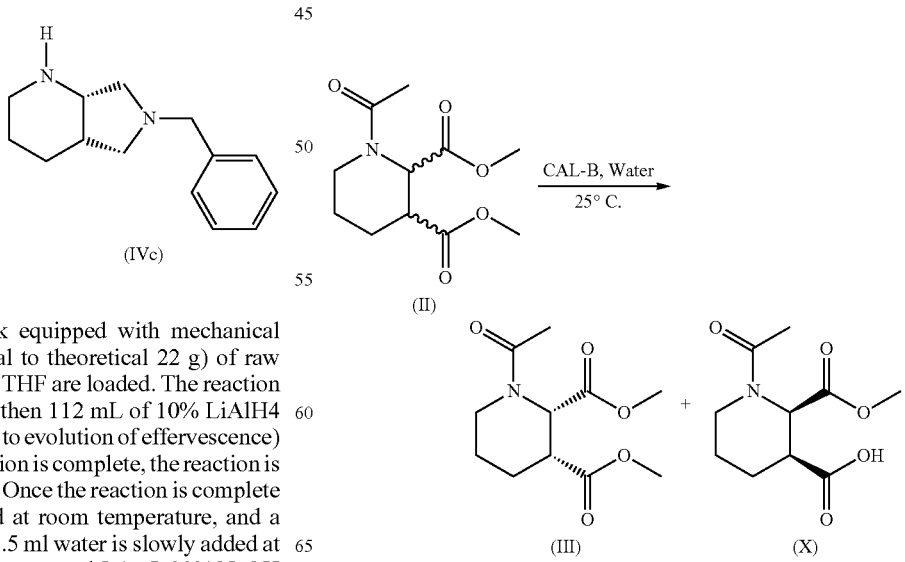

In a 1 L three-necked flask equipped with mechanical stirrer and oil bath, 27 g (equal to theoretical 22 g) of raw intermediate (IVa) and 100 mL THF are loaded. The reaction is stirred at room temperature, then 112 mL of 10% LiAlH4 solution in THF are slowly (due to evolution of effervescence) added dropwise. Once the addition is complete, the reaction is heated for 4 hours under reflux. Once the reaction is complete (followed by GC), it is cooled at room temperature, and a mixture of 135 mL THF and 13.5 ml water is slowly added at 30° C. Then, a mixture of 40 ml water and 5.4 mL 30% NaOH is added. The reaction is stirred for 30 minutes, and the salts In a reactor with mechanical stirrer, thermostat, and automatic titrator loaded with an aqueous solution of 0.1 M NaOH, 50 g cis-1-acetylpiperidine-2,3-dimethyldicarboxylate (intermediate (II)) are loaded in 250 mL of 50 mM phosphate buffered solution at pH 6.3 g of CAL-B free enzyme are added. The reaction is stirred at 25° C. for about 140 hours, maintaining the pH at 6 thanks to the addition of a 0.1 M soda solution. After 140 hours, the diester dimethyl-(2R,3S)-1-acetylpiperidine-2,3-dicarboxylate results to be quantitatively hydrolyzed to the monoacid (intermediate (X)), while the other enantiomer dimethyl-(2S,3R)-1-acetylpiperidine-2,3-dicarboxylate (intermediate (III)) remains unreacted. The work-up already described in example 1 allows obtaining the two enantiomers (intermediate (III) and intermediate (X)) in separate form, in a yield above 97%, a chemical purity above 99% (except for the presence of easily removable inorganic salts), and an optical purity above 99%.

Example 9

Synthesis of the Intermediate (III) (Alk=Me) with Use of Miscible and Immiscible Co-Solvents

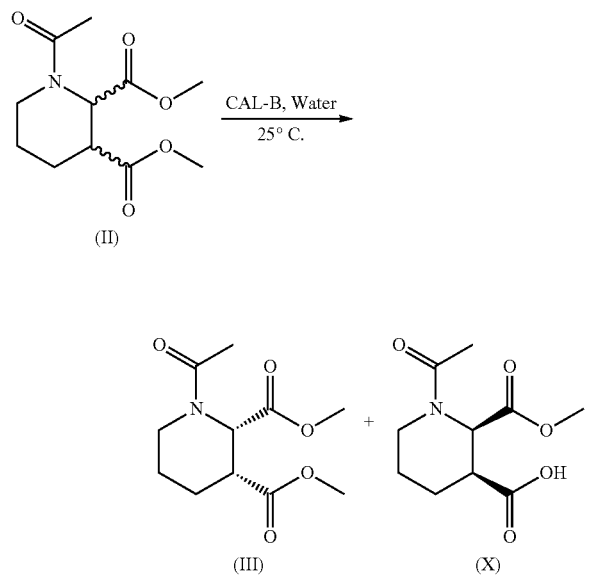

In a reactor with mechanical stirrer, thermostat, and automatic titrator loaded with an aqueous solution of 0.1 M NaOH, 5 g of cis-1-acetylpiperidine-2,3-dimethyldicarboxylate (intermediate (II)) are loaded in 100 ml of 50 mM phosphate buffered solution at pH 6. 10 g CALB-T2-150 Chiralvision covalently immobilized and 0.5 ml Triton (surfactant) are added. The reaction is stirred at 30° C. for about 18 hours maintaining the pH at 6 thanks to the addition of a 0.1 M soda solution. After 18 hours, about 8% of dimethyl-(2R,3S)-1-acetylpiperidine-2,3-dicarboxylate is hydrolyzed to monoacid. The diester enantiomer dimethyl-(2S,3R)-1-acetylpiperidine-2,3-dicarboxylate does not result to be reacted.

A similarly performed test using 5 ml N-methyl-pyrrolidone rather than Triton gave analogous results (7% 2R,3S monoacid after 22 hours)

A further test, performed in an analogous manner and by using 5 ml heptane (mixture of isomers) instead of Triton, brought to the formation of 18% 2R,3S monoacid after 22 hours.

Example 10

Synthesis of the Intermediate (III) (Alk=Me) with Use of Immobilized Enzyme Put in Column (Reaction in Flow)

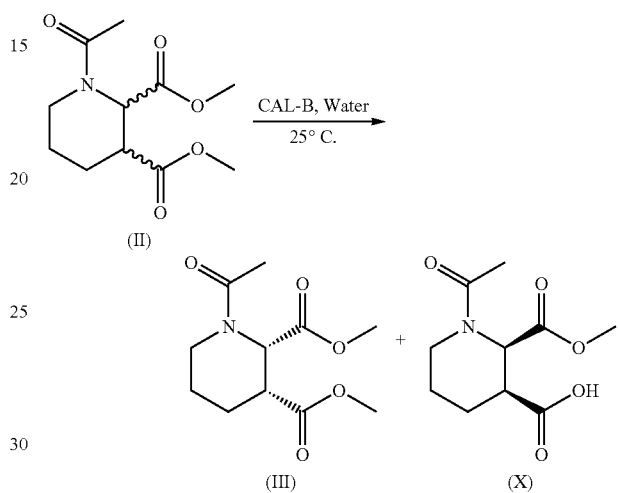

In a thermostated glass column, 50 g covalently immobilized CALB-T2-150 Chiralvision that is hold between two frits is loaded.

In a beaker, equipped with automatic titrator loaded with a 0.1 M NaOH aqueous solution, 5 g cis-1-acetylpiperidine-2,3-dimethyldicarboxylate (intermediate (II)) are loaded in 500 mL of 50 mM phosphate buffered solution at pH 6. The whole system is thermostated at 30° C. Through a pump, that was set to pump 10 mL/minute, the solution is circulated within the column containing the immobilized enzyme. The column outlet brings the solution back in the starting beaker, where the pH is measured continuously and the optional correction is performed. After 18 hour, 70% of 2R,3S enantiomer results to be hydrolyzed to monoacid. The diester dimethyl-(2S,3R)-1-acetylpiperidine-2,3-dicarboxylate results to be unreacted.

In another analogous experiment, which lasted longer, the complete conversion of the diester enantiomer dimethyl-(2R,3S)-1-acetylpiperidine-2,3-dicarboxylate into the respective monoacid (intermediate (X)) was achieved, while leaving the diester dimethyl-(2S,3R)-1-acetylpiperidine-2,3-dicarboxylate (intermediate (III)) unreacted.

Example 11

Synthesis of the Intermediate (III) (Alk=Me) with Use of PLE (Pig Liver Esterase)

In a thermostated vial at 25° C., 1 g of cis-1-acetylpiperidine-2,3-dimethyldicarboxylate (intermediate (II)) is loaded in 10 ml of 50 mM phosphate buffered solution at pH 6. 100 mg of Fluka PLE (pig liver esterase) free enzyme are added.

The reaction is stirred at 25° C. for about 36 hours maintaining the pH at 6 thanks to the addition of 0.1 M soda. The course of the reaction is followed via chiral HPLC.

The enzyme hydrolyzes preferentially the enantiomer dimethyl-(2S,3R)-1-acetylpiperidine-2,3-dicarboxylate, providing the intermediate (2S,3R)-1-acetyl-2-(methoxycarbonyl)piperidine-3-carboxylic acid of formula (X-bis)

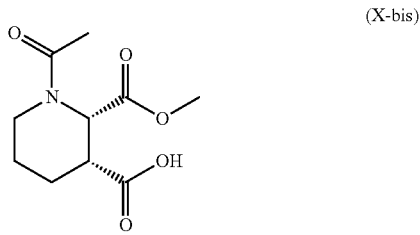 [SMILES: COC(=O)[C@@H]1[C@H](C(=O)O)CCCN1C(C)=O]

(X-bis)

leaving the diester dimethyl-(2R,3S)-1-acetylpiperidine-2,3-dicarboxylate of formula III-bis

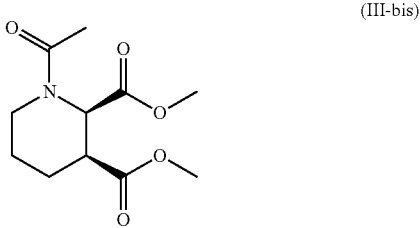 [SMILES: COC(=O)[C@H]1CCCN(C(C)=O)[C@H]1C(=O)OC]

(III-bis)

partially unreacted.

The isolated compound (X-bis), like his enantiomer (X), undergoes to the conversion according the following scheme

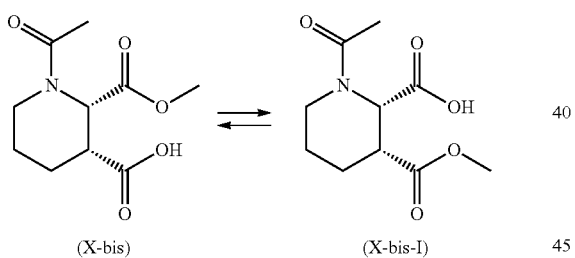

(X-bis)  (X-bis-I)

providing the compound (2S,3R)-1-alkylcarbonyl-3-(alkoxycarbonyl)piperidine-2-carboxylic acid of formula X-bis-1.

The invention claimed is:

1. A (2S,3R)-1-alkylcarbonylpiperidin-2,3-dialkyldicarboxylate compound of formula (III):

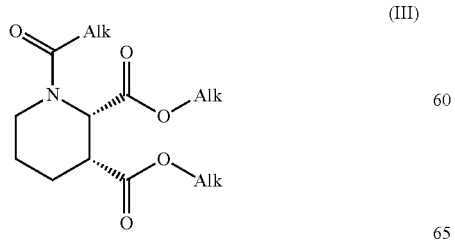

(III)

in which Alk is a straight or branched C1-C5 alkyl group.

2. The compound according to claim 1, having a proton NMR spectrum in CDCl3 and at 300 MHz as shown in FIG. 1, and a 13C NMR spectrum in CDCl3 and at 300 MHz as shown in FIG. 2.

3. A compound (2R,3S)-1-alkylcarbonyl-2-(alkoxycarbonyl)piperidine-3-carboxylic acid of formula (X):

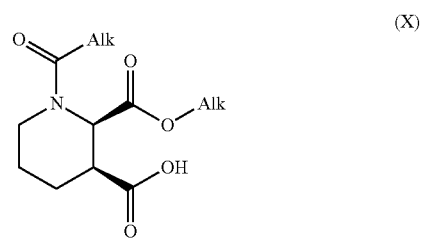

(X)

in which Alk is a straight or branched C1-C5 alkyl group.

4. The compound according to claim 3, having an IR spectrum as shown in FIG. 3 and a proton NMR spectrum in CDCl3 and at 300 MHz as shown in FIG. 4.

5. Compound of any of formulas:
(X-bis) named (2S,3R)-1-alkylcarbonyl-2-(alkoxycarbonyl)piperidine-3-carboxylic acid:

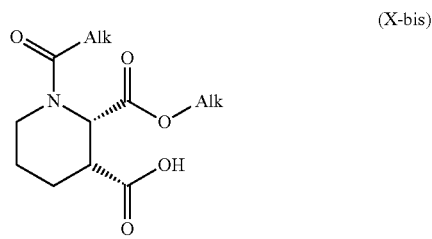

(X-bis)

(X-bis-I) named (2S,3R)-1-alkylcarbonyl-3-(alkoxycarbonyl)piperidine-2-carboxylic acid:

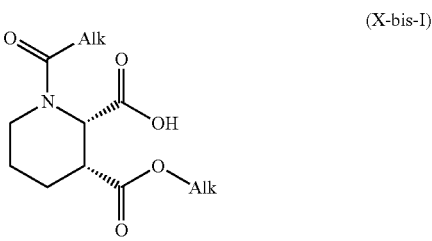

(X-bis-I)

(IV) named (4aR,7aS)-1-alkylcarbonylhexahydrofuro[3,4-b]pyridine-5,7-dione:

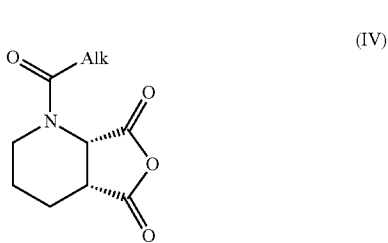

(IV)

(IVa) named 6-substituted-(4aR,7aS)-1-alkylcarbonyltetrahydro-1H-pyrrolo[3,4-b]pyridine-5,7(2H,6H)-dione:

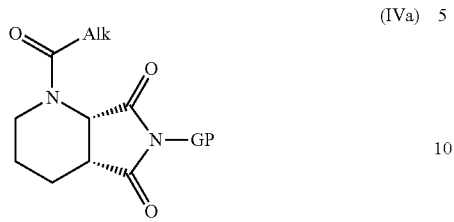
(IVa)

in which Alk is a straight or branched C1-C5 alkyl group and GP is a protecting group selected from benzyl or benzyl substituted with alkyl, p-nitro, fluoro, trifluoromethyl in the ortho or para positions.

6. Compound according to claim 1, where Alk is methyl.

7. Compound according to claim 1, where Alk is a straight or branched C1-C5 alkyl group and the Alk group of the ester functional group can be the same or different of Alk of the amidic function group on nitrogen in position 1.

* * * * *